United States Patent [19]

Rota et al.

[11] Patent Number: 5,316,910

[45] Date of Patent: May 31, 1994

[54] BIOASSAY FOR INFLUENZA A AND B NUCLEOPROTEIN

[75] Inventors: Paul A. Rota, Decatur; Renee A. Black, Doraville, both of Ga.

[73] Assignee: The United States of America as represented by the Secretary of the Department of Health and Human Services, Washington, D.C.

[21] Appl. No.: 15,739

[22] Filed: Feb. 10, 1993

Related U.S. Application Data

[62] Division of Ser. No. 670,791, Mar. 19, 1991, abandoned.

[51] Int. Cl.$^5$ .............................................. C12Q 1/00
[52] U.S. Cl. ...................................... 435/7.1; 435/5; 435/7.92; 435/69.1; 435/69.3; 435/7.2; 435/7.21
[58] Field of Search ............. 435/69.1, 7.1, 7.2, 435/7.21, 172.1, 172.3, 320.1; 536/23.1, 23.72

[56] References Cited

PUBLICATIONS

Roitt, "Essential Immunology", 4th Ed., 1980, Blockwell Scientific Publications, pp. 144–151.
Rota, P. A., "Sequence of a cDNA clone of the nucleoprotein gene of influenza B/Ann Arbor/1/86," Nucleic Acids Res., vol. 17, No. 9, 1989.
Townsend, A. R. M., et al., "The Influenza A Virus Nucleoprotein Gene Controls the Induction of Both Subtype Specific and Cross-Reactive Cytotoxic T Cells," J. Experimental Medicine 160:552–563 (1984).
Wraith, D. C., et al., "Purified Influenza Virus Nucleoprotein Protects Mice from Lethal Infection," J. Gen. Virol. 68:433–440 (1987).
Van Wyke, K. L., et al., "Antigenic Variation of Influenza A Virus Nucleoprotein Detected with Monoclonal Antibodies," J. Virol. 35:24–30 (1980).
Schmaljohn, C. S., et al., "Baculovirus Expression of the Small Genome Segment of Hantaan Virus and Potential Use of the Expressed Nucleocapsid Protein as a Diagnostic Antigen," J. Gen. Virol 69:777–786 (1988).
Harmon, M. W., et al., "Immunoassay for Serologic Diagnosis of Influenza Type A Using Recombinant DNA Produced Nucleoprotein Antigen and Monoclonal Antibody to Human IgG," J. Med. Virol. 27:25–30 (1989).
Luckow, V. A., et al., "Trends in the Development of Baculovirus Expression Vectors," Bio/Technology 6:47–55 (1987).
Possee, R. D., "Cell-surface expression of influenza virus haemagglutinin in insect cells using a baculovirus vector," Virus Res. 5:43–59 (1986).

(List continued on next page.)

Primary Examiner—Richard A. Schwartz
Assistant Examiner—David Guzo
Attorney, Agent, or Firm—Townsend and Townsend Khourie and Crew

[57] ABSTRACT

The present invention relates to nucleoprotein (NP) genes of the influenza A and B viruses which were constructed from virion RNA and subsequently expressed in Spodoptera frugiperda (S19) cells using the baculovirus vector, Autographa californica nuclear polyhedrosis virus (AcNPV). Western blot analysis of lysates prepared from S19 cells infected with the recombinant viruses confirmed that the baculovirus-expressed NP antigens were reactive with monoclonal antibodies specific for either type A or B NP and with anti-NP antibodies in human serum samples. Electrophoretic analysis indicated that the expressed influenza NP antigens comigrated with NP purified from influenza A or B virions and that the recombinant NP antigens represented greater than 10% of total protein in infected cells. Dilutions of clarified S19 cell lysates were used as antigens in a standard enzyme immunoassay format to detect serum antibody specific for influenza A or B viruses. The results from assays using the baculovirus-expressed NP antigens showed good correlation with the results obtained using bacterially-expressed NP antigen as well as complement fixation. Therefore, baculovirus-expressed NP antigens can be used in reproducible and routine assays for the serodiagnosis of influenza virus infections as an alternative to the more burdensome complement fixation or hemagglutination tests.

9 Claims, 9 Drawing Sheets

OTHER PUBLICATIONS

Doller, et al., "The Safety of Insect Viruses as Biological Control Agents," in *Viral Insecticides for Biological Control,* Eds. Maramorosch and Sherman, Acad. Press, N.Y., pp. 399–439 (1985).

Cox, N.J., et al., "Identification of Sequence Changes in the Cold–Adapted, Live Attenuated Influenza Vaccine Strain, A/Ann Arbor/6/60 (H2N2)," *Virology* 167:554–567 (1988).

Rota, P. A., et al., "Expression of influenza A and B virus nucleoprotein antigens in baculovirus," *J. Gen. Virol.* 71:1545–1554 (1990).

Harley, V. R., et al., "Characterisation of an avian influenza virus nucleoprotein expressed in *E. coli* and in insect cells," *Arch Virol* 113:267–277 (1990).

Matsuura, Y., et al., "Baculovirus Expression Vectors: the Requirements for High Level Expression of Proteins, Including Glycoproteins," *J. Gen. Virol.* 68:1233–1250 (1987).

BIOASSAY FOR INFLUENZA A AND B NUCLEOPROTEIN

This is a divisional of application Ser. No. 07/670,791, filed Mar. 19, 1991, now abandoned.

BACKGROUND OF THE INVENTION

1. Field of the Invention

The present invention relates to baculovirus-expressed influenza antigens, in particular, to the influenza A and B viral nucleoprotein antigens expressed from *Autographa californica* nuclear polyhedrosis virus (AcNPV). The invention further relates to bioassays for the detection of influenza viral infections and to the use of such proteins in vaccines against influenza A or B virus.

2. Background Information

The nucleoprotein (NP) is the major protein component of the ribonucleoprotein core of influenza virions and is a type-specific antigen defining influenza viruses as either type A or type B. Recent studies have also identified the nucleoprotein antigen as a major target of the cross-reactive cytotoxic T-cell response against influenza viruses (Townsend et al., 1984, *Journal of Experimental Medicine* 160, 552-583); therefore, cellular immunity to NP may contribute to recovery from influenza infection (Wraith et al., 1987, *Journal of General Virology* 68, 433-440).

As antigenic variation of NPs occurs more slowly than does that of influenza surface glycoproteins (Van Wyke et al., 1980, *Journal of Virology* 35, 24-30), the NP is particularly useful for serodiagnostic tests for the detection of influenza infections in mammals. The test for measuring antibodies to NP has traditionally been a complement fixation (CF) test. However, the CF test has several drawbacks. For example, the CF test requires that a large number of biological reagents be standardized. In addition, the NP antigen preparations used in the CF test are likely to contain other virus-specific antigens. Serodiagnostic tests which overcome these drawbacks would be valuable tools for the detection of influenza infections.

Since the NP antigen is antigenically conserved, it is an ideal candidate for expression by recombinant DNA methodology as part of the development of a new generation of diagnostic assays for influenza virus infections. Viral antigens produced by recombinant DNA expression systems can provide an inexhaustible source of chemically defined material for use in serodiagnostic assays, experimental vaccines, and fundamental research. These techniques also eliminate the costs and potential hazards in the large-scale cultivation of pathogenic viruses. For example, the use of baculovirus-expressed Hantaan virus nucleoprotein as a diagnostic antigen has been reported recently (Schmaljohn et al., 1988, *Journal of General Virology* 69, 777-786). Further, the use of NP antigen produced in *Escherichia coli* (*E. coli*) in an experimental diagnostic assay for influenza A has been reported (Harmon et al., 1989, *Journal of Medical Virology* 24, 25-30). This assay was found to be superior to CF for influenza virus diagnosis.

The recently developed eucaryotic expression system using recombinant baculovirus, *Autographa californica* nuclear polyhedrosis virus (AcNPV), should be useful for producing antigens for immunoassays for the serologic diagnosis of viral infections (Luckow et al., 1987, *Bio/Technology* 6, 47-55). Infecting insect cells (*Spodoptera frugiperda*) with such recombinant baculoviruses allows for the production of large amounts of antigen (Possee, R. D., 1986, *Virus Research* 5, 43-59). In addition, the baculovirus system has other important advantages over the commonly used methods of producing viral antigens. For example, with the baculovirus system the viral antigens are produced in cells that do not contain antigens that cross-react with antibodies in most human serum. Therefore, the purification of the antigen that is required for proteins expressed in bacterial and yeast systems may not be required with baculovirus-expressed antigens. Further, baculoviruses do not infect humans and can therefore be safely handled in large quantities.

SUMMARY OF THE INVENTION

It is an object of the present invention to provide a less costly, easier and safer means of producing influenza A and B NP antigens than provided with previous methods.

It is another object of the present invention to provide baculovirus-expressed nucleoproteins from influenza A and B viruses for use in serodiagnostic assays for influenza virus.

It is a further object of the present invention to provide serodiagnostic assays for the detection and diagnosis of influenza A and B viral infections.

Various other objects and advantages of the present invention will become apparent from the drawings and the following detailed description of the invention.

In one embodiment, the present invention relates to a DNA construct comprising a DNA segment encoding a nucleoprotein of influenza A or influenza B virus; and a vector comprising a polyhedrin gene promoter from a baculovirus, baculovirus flanking sequences and a bacterial origin of replication. The DNA segment of the construct is operably linked to the polyhedrin gene promoter of the vector.

In another embodiment, the present invention relates to recombinant baculoviruses and to host cells infected therewith. Recombinant baculoviruses to which the present invention relates encode a nucleoprotein of influenza A or influenza B virus. Host insect cells of the present invention are infected with a recombinant baculovirus in a manner allowing the expression of the NP encoded in the baculovirus.

In another embodiment, the present invention relates to baculovirus-expressed influenza A or influenza B virus nucleoprotein and to a method of producing the baculovirus-expressed influenza A or B virus nucleoprotein. Baculovirus-expressed influenza A or B virus nucleoproteins are produced by culturing host insect cells of the present invention, in a manner allowing the expression of the nucleoprotein encoded in the infecting baculovirus, and isolating the nucleoprotein from the cells.

In a further embodiment, the present invention relates to a bioassay for the diagnosis of influenza in mammals comprising the steps of coating a surface with the baculovirus-expressed nucleoprotein of the present invention, contacting the coated surface with a biological sample from a mammal suspected of having influenza, and detecting the presence or absence of a complex formed between the protein and antibodies specific therefore present in the biological sample. The present invention also relates to diagnostic kits comprising the baculovirus-expressed nucleoprotein and ancillary reagents suitable for use in detecting the presence or absence of antibodies to the protein in a biological sample.

In yet a further embodiment, the present invention relates to a vaccine for mammals against influenza A or influenza B virus. The vaccine comprises the baculovirus-expressed nucleoprotein of the present invention, in an amount sufficient to induce immunization against the virus, and a pharmaceutically acceptable carrier.

DETAILED DESCRIPTION OF THE INVENTION

The present invention relates to a system for expressing influenza A and B NP antigens utilizing baculoviruses and to the proteins made therewith. NP proteins to which the present invention relates react specifically with anti influenza NP antibodies and, therefore, can be used in serodiagnostic assays. The present invention provides an easier and safer means of producing influenza virus NPs and is less costly than current methods. For example, the present invention is safer than the isolation of NP from whole virus as the recombinant viruses of the present invention are not infectious for mammals. In addition, the NP antigens of the present invention do not need further costly purification in order to separate them from other proteins which react strongly with human serum. Such separation is necessary for NP antigens produced in bacterial systems.

In one embodiment, the present invention relates to a DNA construct encoding a NP antigen of an influenza A or B virus. The DNA construct comprises a DNA segment encoding a NP of an influenza A or influenza B virus and a vector. The vector comprises the polyhedrin gene promoter region of a baculovirus, the baculovirus flanking sequences necessary for proper cross-over during recombination (the flanking sequences comprise about 200-300 base pairs adjacent to the promoter sequence) and a bacterial origin of replication which permits the construct to replicate in bacteria. The vector is constructed so that (i) the DNA segment is placed adjacent (or operably linked or "downstream" or "under the control of") to the polyhedrin gene promoter and (ii) the promoter-NP antigen combination is flanked on both sides by 200-300 base pairs of baculovirus DNA (the flanking sequences). Suitable vectors for use in the present invention include, but are not limited to, pAcYM1.

To produce the DNA construct of the present invention, a cDNA clone encoding the full length NP of an influenza A or influenza B virus is obtained using methods known in the art and inserted into a plasmid, such as, for example, pUC 8. Then plasmid containing the NP gene is then ligated into a transfer vector, for example, pAcYM1, to yield the DNA construct.

The DNA construct of the present invention is used to generate recombinant baculoviruses. The DNA construct is contacted in a host cell with baculovirus DNA of an appropriate baculovirus (that is, of the same species of baculovirus as the promoter encoded in the construct) under conditions such that recombination is effected. The resulting recombinant baculoviruses encode either the full length influenza A virus NP or influenza B virus NP. For example, an insect cell can be cotransfected or transfected separately with a DNA construct of the present invention and a functional baculovirus. Resulting recombinant baculoviruses can then be used to infect insect cells to effect production of the NP protein.

In another embodiment, the present invention relates to host insect cells, for example, Spodoptera frugiperda cells, producing a baculovirus-expressed influenza NP. Insect host cells infected with a recombinant baculovirus of the present invention and cultured under conditions allowing expression of the baculovirus-encoded NP produce baculovirus-expressed NP antigens. NPs thus produced are then isolated from the cells using methods known in the art. Further, it is contemplated that host cells can be stably transformed with the DNA constructs of the present invention.

The baculovirus-expressed influenza nucleoproteins of the present invention may be more reactive than the previously described bacterially-expressed ANP (Harmon et al., 1989, Journal of Medical Virology 24, 25–30). The bacterially-expressed antigen is a fusion protein which contains part of a bacterial protein. The baculovirus-expressed NPs are complete copies of the viral NP genes and no additional amino acids have been added. The bacterially-expressed ANP showed decreased reactivity compared to viral NP on Western blot analysis. Unexpectedly, no decrease in reactivity was observed when the baculovirus-expressed NPs were analyzed in the same manner. Accordingly, the NP antigens of the present invention should provide a more reactive material for use in bioassays and vaccines to detect and prevent influenza A and/or B viral infections.

In another embodiment, the present invention relates to bioassays for the diagnosis of influenza virus infections in mammals. Using standard diagnostic protocols the baculovirus-expressed nucleoproteins of the present invention can be used to detect the presence of antibodies specific therefore in biological samples without undue experimentation.

For example, by coating a solid surface such as a polystyrene microtitration plate, a slide or nylon or nitrocellulose membranes generated by immunoblot or Western blot, with the baculovirus-expressed NP of the present invention and contacting the surface with a biological sample, such as serum, the presence or absence of antibodies to the influenza A or B virus can be detected. If antibodies are present in the sample formation of antibody-protein complexes is effected. These complexes can be detected using standard methodologies known in the art. As the NP of the present invention appears more reactive than the bacterially-produced NP smaller amounts may be needed in the bioassay. Further, the bioassays may be more accurate due to this additional reactivity.

For a general diagnosis of an influenza infection the solid surface is coated with both the influenza A NP and influenza B NP of the present invention. For the determination of a specific type of influenza infection (that is, an influenza A or B viral infection), the solid surface is coated with either the influenza A NP or the influenza B NP of the present invention.

The present invention further relates to diagnostic kits. The diagnostic kits of the present invention comprise the baculovirus-expressed NP antigens of the present invention and ancillary reagents suitable for use in detecting the presence or absence of antibodies or the DNA constructs of the present invention necessary for production of the NP and ancillary reagents.

In a further embodiment, the present invention relates to vaccines for mammals against influenza A or influenza B viral infections. Protective antibodies against influenza can be raised by administering to a mammal a vaccine comprising the baculovirus expressed nucleoproteins of the present invention in a pharmaceutically acceptable carrier. The baculovirus expressed NP antigen is present in the vaccine in an amount sufficient to induce immunization against the virus. As one skilled in the art will understand, it is not necessary to use the entire protein. A unique, antigenic portion of the influenza nucleoprotein can be used. Vaccines of the present invention can also include effective amounts of immunological adjuvants known to enhance an immune response.

The following examples are given to further illustrate the present invention without being deemed limitative thereof.

EXAMPLES cDNA cloning of influenza type A and B NP genes.

Virion RNA was extracted from gradient purified influenza B/Ann Arbor/1/86 and A/Ann Arbor/6/60 (wild-type) viruses by standard methods (Cox et al., 1983, Bulletin of the World Health Organization 61, 143–152). cDNA copies of total viral RNA were prepared by the method of Lapeyre and Amairic (Lapeyre et al., 1985, Gene 37, 215–220) except that first-strand synthesis by reverse transcriptase was primed by using universal influenza type A or B primers complementary to the 3' untranslated region of virion RNA. The double-stranded cDNA fragment corresponding to influenza genomic RNA segment 5 (influenza A: 1565 base pairs; influenza B: 1811 base pairs) was isolated from agarose gels, purified, and ligated into the Sma I site of plasmid pUC 8 using standard methods (Maniatis et al., 1982. Molecular Cloning: A Laboratory Manual. Cold Spring Harbor Laboratory, Cold Spring Harbor, N.Y.) Bacterial colonies (E. coli, HB101) containing recombinant plasmids with NP inserts were identified by in situ hybridization (Maniatis et al., (1982). Molecular Cloning: A Laboratory Manual. Cold Spring Harbor Laboratory, Cold Spring Harbor, N.Y.) to $^{32}$P-labeled, oligonucleotide primers with sequences specific for influenza A or B NP genes.

Figure 1:
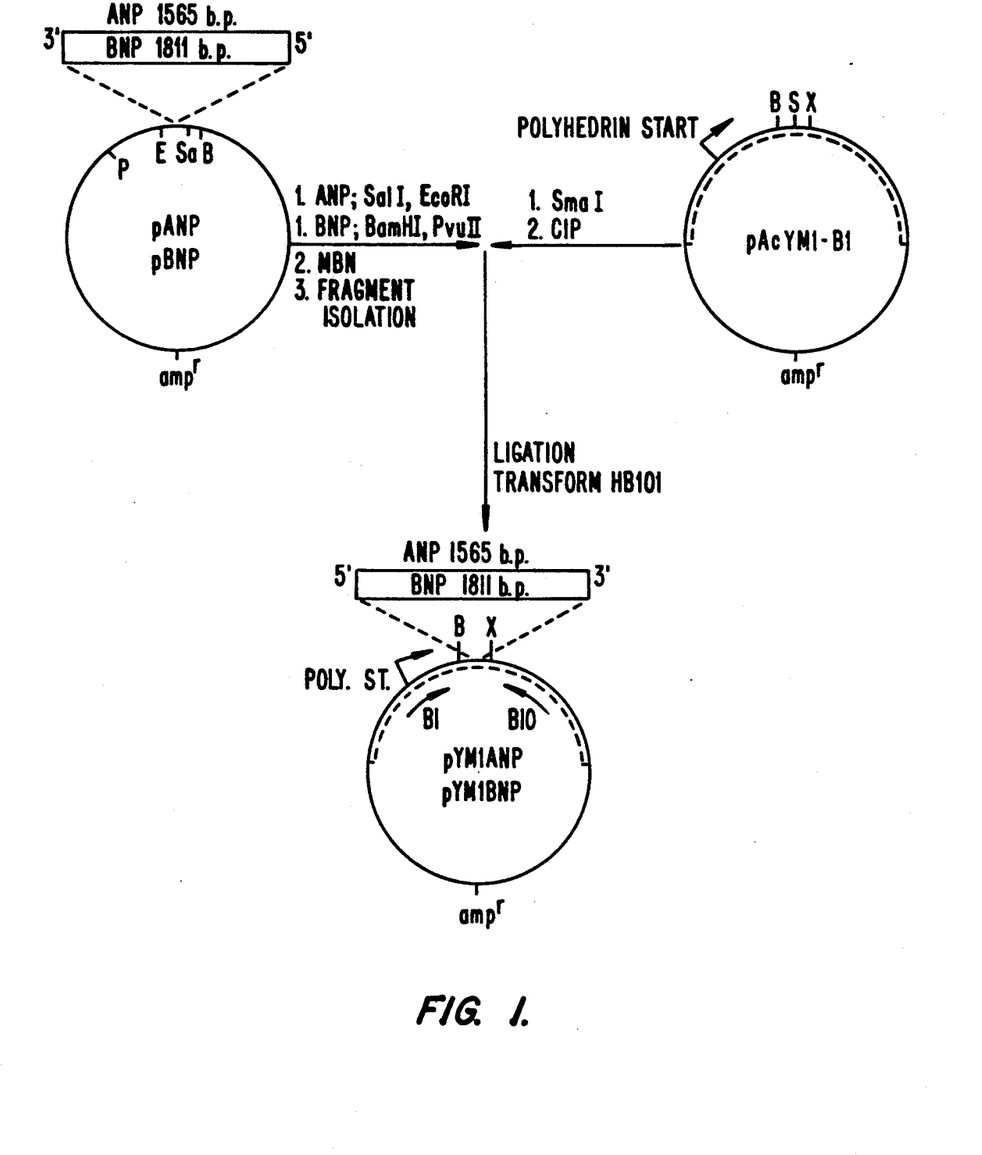
FIG. 1 shows the construction scheme of baculovirus transfer vectors. Solid black lines indicate plasmid DNA and black lines with dashed inner lines indicate AcNPV DNA. Abbreviations are S: SmaI, P: PvuII, B: BamHI, Sa: SalI, E: EcoRI, X: Xba I, CIP: calf intestinal phosphatase, MBN: mung bean nuclease. Arrows indicate the start site of AcNPV polyhedrin gene mRNA and binding regions of the B1 and B10 sequencing primers.
Figure 2A:
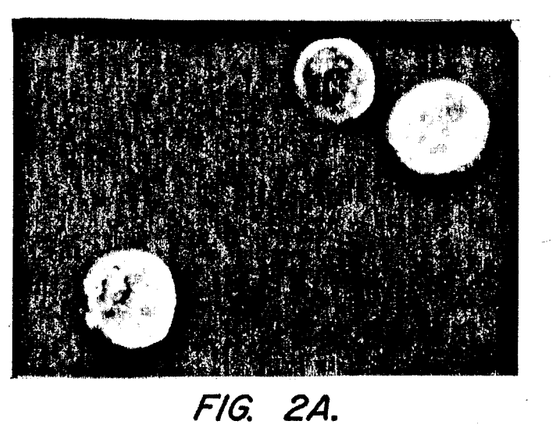
FIG. 2 demonstrates detection of baculovirus-expressed influenza A or B NP by fluorescent antibody. Sf9 cells were infected with AcANP (A), AcBNP(C) or wild type AcNPV (B) fixed and stained with FITC-conjugated monoclonal antibody to type A NP (A, B) or type B NP (C, D). Magnification was 400x.
Figure 2B:
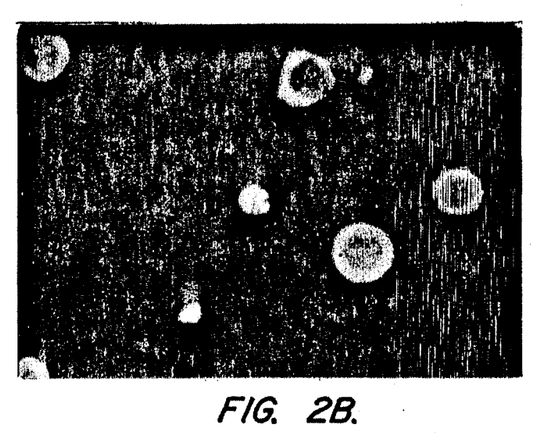
Figure 2C:
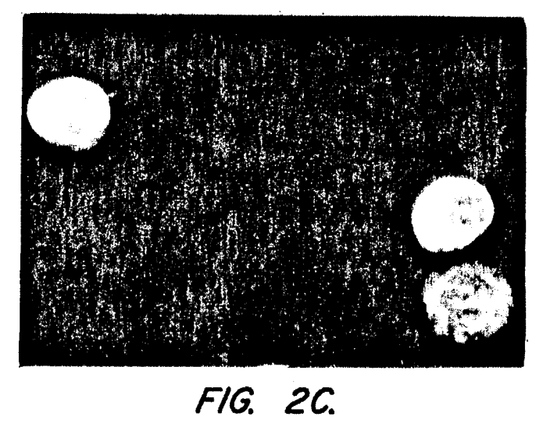
Figure 2D:
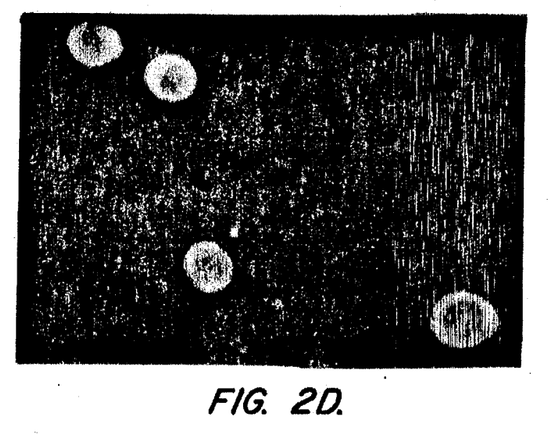
Figure 3A:
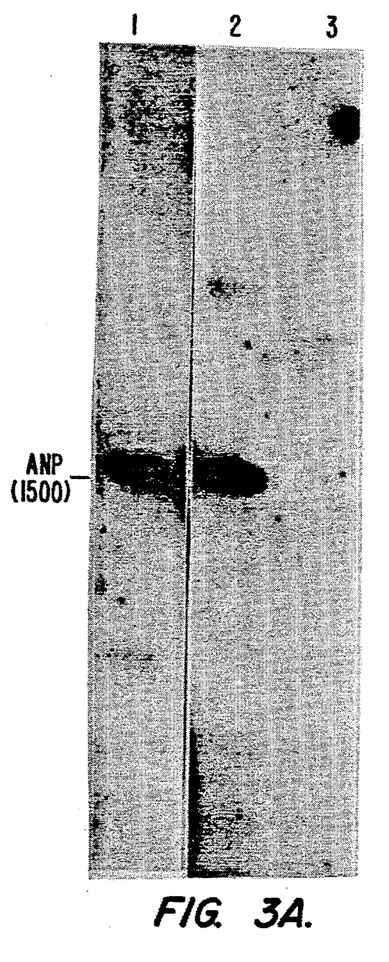
FIG. 3 demonstrates the detection of influenza A or B NP genes in recombinant baculovirus. DNA from pANP (A) or pBNP (B) (lane 1), AcANP or AcBNP (lane 2) and wild type AcNPV (lane 3) was digested with SalI and EcoRI (A) or BamHI and PvuII (B) separated by agarose gel electrophoresis, transferred to nitrocellulose and hybridized to $^{32}P$-labeled primers specific for either A NP (A) or B NP (B).
Figure 3B:
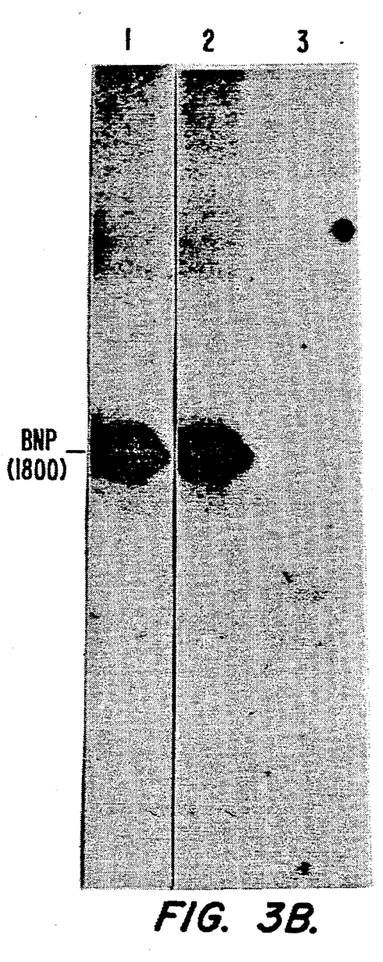
Figure 4A:
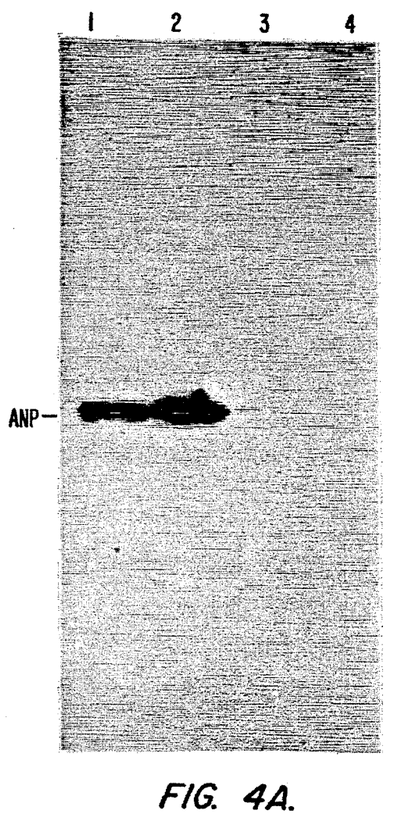
FIG. 4 shows a Western blot analysis of baculovirus-expressed influenza A or B NP antigens. Samples are purified influenza A (A) or B (B) virions (lane 1) or lysates of cells infected with wild-type AcNPV (lane 4), AcANP (A2, B3), and AcBNP (B2, A3). Samples were electroblotted after electrophoresis and hybridized to monoclonal antibodies specific for A NP (A) or B NP (B).
Figure 4B:
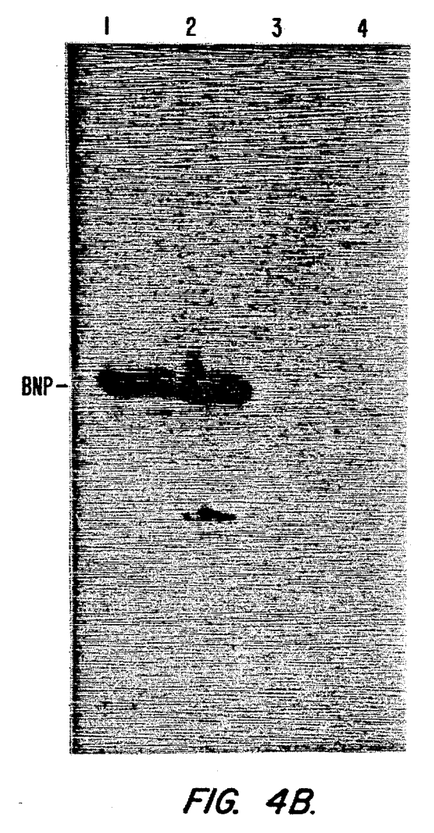
Figure 5A:
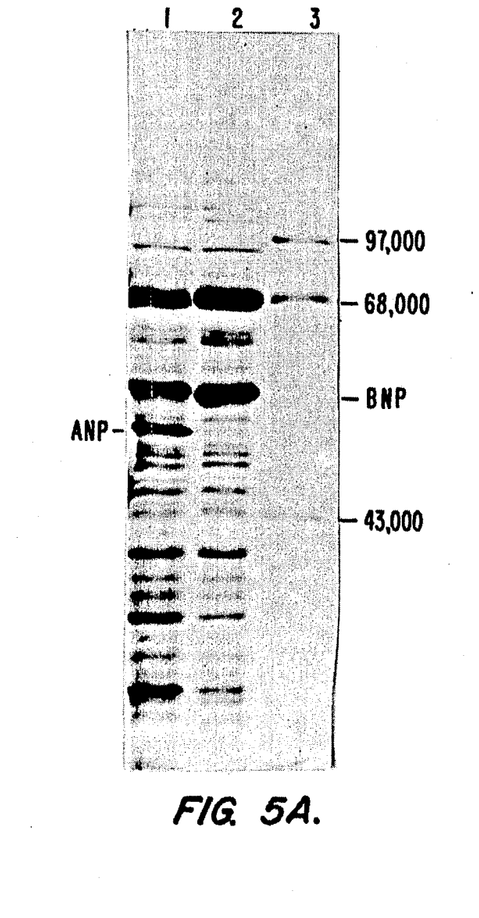
FIG. 5. Panel A shows Coomassie Blue-stained gel from FIG. 4. Lanes 1 and 2 are lysates of Sf9 cells infected with AcANP (1) or AcBNP (2); lane 3 contains molecular-weight markers. Bands identified as either A or B NP by immunological staining are marked. Panel B shows spectrodensitometric scans of the gels from panel A.
Figure 5B:
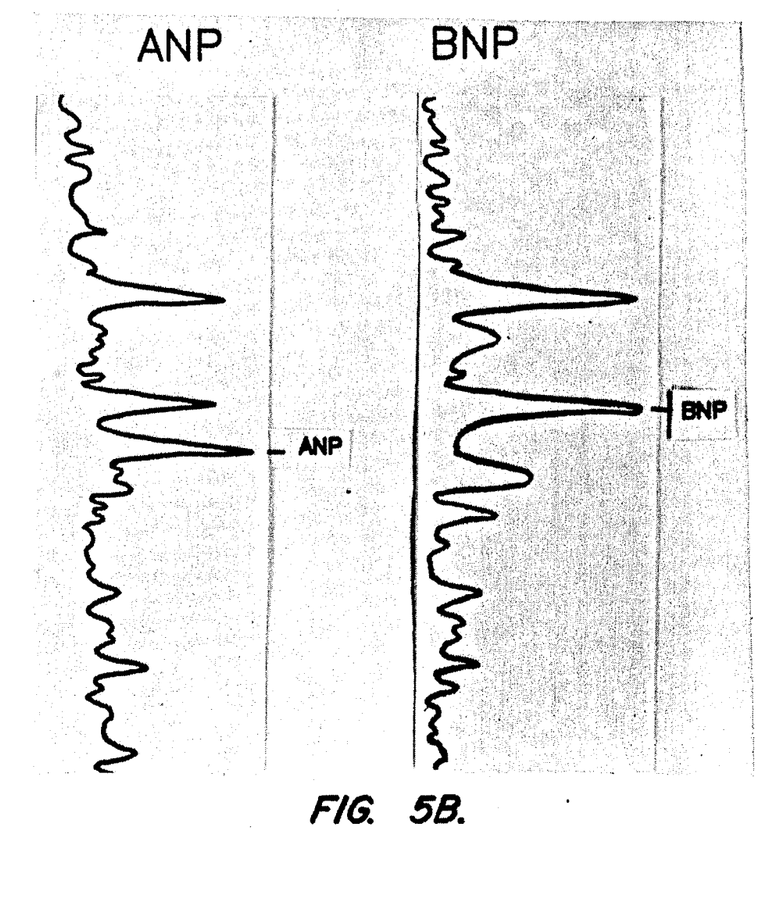

The size, sequence, and orientation of the inserted NP genes were determined by a rapid plasmid-sequencing technique (Chen et al., 1985, DNA 4, 165–171) using the M13 forward and reverse primers and by restriction endonuclease analysis. (The complete nucleotide sequences of both NP genes have been published see Cox et al., 1983, Bulletin of the World Health Organization 61, 143–152 and Rota, P.A., 1989, Nucleic Acids Research 17, 3595). Plasmids containing full-length cDNA copies of the influenza A and B NP genes were designated pANP and pBNP, respectively (FIG. 1). The A NP cDNA clone was 1565 bases in length; the B NP was 1811. Both clones contained the entire NP coding sequence and 5' untranslated region, and both NP genes were oriented in the pUC plasmids with the 5' end of the gene closest to the BamHI site on the pUC polylinker (FIG. 1).

Expressions of influenza nucleoproteins in insect cells.

Influenza A and B NP genes were excised from pANP and pBNP by restriction endonuclease digestion, purified by agarose gel electrophoresis, made blunt-ended by treatment with mung bean nuclease, and ligated into the Sma 1 site of the transfer vector, pAcYM1B1 (FIG. 1). pAcYM1B1, a derivative of pAcYM1 (Matsuura et al., 1987, *Journal of General Virology* 68, 1233-1250) contains a multiple cloning site inserted at the unique Bam H1 site of pAcYM1 (gift of Anthony Sanchez, Centers for Disease Control, Atlanta, Ga.).

Transformant colonies containing the inserted NP genes were identified by in situ hybridization as mentioned earlier. The proper orientation of the NP genes with respect to the AcNPV polyhedrin gene promoter was confirmed by sequencing purified plasmid DNA using oligonucleotide primers, B1 and B10 (also a gift of Anthony Sanchez, Centers for Disease Control, Atlanta, Ga.), designed to sequence the 5' and 3' termini of DNA fragments inserted into the multiple cloning site of pAcYM1B1 (FIG. 1).

The sequences also indicated that the translation start sites of the A and B NPs were, respectively, 50 and 58 bases downstream from the deleted translation start site on the AcNPV polyhedrin gene (Matsuura et al., 1987, *Journal of General Virology* 68, 1233-1250) and therefore 100 and 108 bases downstream of the transcription start site of the AcNPV polyhedrin gene mRNA.

Insect cell culture and propagation of AcNPV were done by using previously described methods (Summers et al., 1987, *Texas Agricultural Experiment Station Bulletin* No. 1555). Purified pYM1ANP and pYM1BNP DNA were each cotransfected with purified AcNPV DNA into Spodoptera frugiperda (Sf9, ATCC CRL 1711) cells according to the protocol described by (Summers et al., 1987, *Texas Agricultural Experiment Station Bulletin* No. 1555).

After 5 to 6 days of incubation, serial dilutions ($10^{-3}$ to $10^{-8}$) of the culture supernatants were prepared in Hink's medium, and 20 ul amounts of each dilution were inoculated into Sf9 cells that had been seeded into 96-well tissue-culture plates. The supernatants from each well, harvested after 5 to 6 days, were transferred to a sterile 96-well plate for storage and the remaining cells were resuspended in 100 ul of phosphate-buffered saline (PBS), lysed by freezing and thawing, and spotted onto nitrocellulose filters.

Cultures expressing influenza A or B NP were detected by incubating the filters with either influenza A or B NP-specific monoclonal antibodies (Walls et al., 1986, *Journal of Clinical Microbiology* 23, 240-245). Hybridization and wash conditions were identical to those used for Western blot analysis (Tsang et al., 1983, *Methods in Enzymology* 92, 377-391) except that bound antibody was visualized with $^{125}$I-Staphylococcal protein A. Recombinant viruses expressing either the influenza A or B NP were purified from cultures that were strongly positive for antigen expression by three successive rounds of plaque isolation (Summers et al., 1987, *Texas Agricultural Experiment Station Bulletin* No. 1555). Only plaques that were negative for polyhedrin gene expression by light microscopic examination were selected.

Sf9 cells infected with the recombinant viruses were removed from the culture vessel, washed with Grace's medium, fixed onto microscope slides with ice-cold acetone and examined by fluorescent antibody assay using fluorescein-isothiocynate (FITC)-conjugated influenza A or B NP-specific monoclonal antibodies (Boots-Celltech, Berks, U.K.) (Walls et al., 1986, *Journal of Clinical Microbiology* 23, 240-245). Evaluation of the baculovirus recombinant with a fluorescent antibody assay was repeated after plaque purification of the recombinant viruses, AcANP and AcBNP (FIG. 2). Cells infected with purified recombinant baculovirus showed intense, granular fluorescence when stained with FITC-conjugated monoclonal antibodies specific for either influenza A or B NP. In some cases large, positively staining aggregates were visible in the cytoplasm of the infected cells. Sf9 cells infected with wild-type AcNPV gave little background fluorescence.

Analysis of recombinant baculoviruses.

DNA from the plaque-purified recombinant baculoviruses, AcANP and AcBNP, was extracted from the cytoplasm of infected Sf9 cells and analyzed by restriction endonuclease digestion and Southern blot hybridization by standard procedure (Maniatis et al. (1982). Molecular Cloning: A Laboratory Manual. Cold Spring Harbor Laboratory, Cold Spring Harbor, N.Y.).

The Southern analyses of the purified DNA from Sf9 cells is shown in FIG. 3. Restriction fragments that comigrated with NP genes excised from the pUC plasmids and also hybridized to influenza A or B NP-specific $^{32}$P-labeled oligonucleotide probes were detected in the blots of restriction digests of DNA from AcANP and AcBNP. Therefore the recombinant baculoviruses appeared to contain complete copies of the appropriate NP genes.

Lysates prepared from infected cells were subjected to electrophoresis on 10% polyacrylamide gels containing 4M urea (Lamb et al., 1978, *Virology* 91, 60–78) followed by Western blot analysis (Tsang et al., 1983, *Methods in Enzymology* 92, 377–391). To quantitate the amount of influenza A or B NP contained in cell lysates, gels containing electrophoretic separations were stained with Coomassie brilliant blue and the amount of NP protein present determined by scanning densitometry.

Western blot analysis of total cell lysates prepared from Sf9 cells infected with either the A or the B NP-producing recombinant virus indicated that the NP antigens being expressed by the recombinant viruses were recognized by influenza A or B NP-specific monoclonal antibodies and had electrophoretic mobilities that were identical to those of NPs contained in purified influenza A or B virions (FIG. 4). The monoclonal antibodies did not cross-react with any other antigens contained in Sf9 cell lysate or with the NP antigen of the heterologous subtype. In this gel system, the A NP migrated with an apparent molecular weight of approximately 53 kilodaltons while the B NP was slightly larger, approximately 58 kilodaltons (FIG. 5). Electrophoretic separations of lysates from infected Sf9 cells were also stained with Coomassie brilliant blue and analyzed by scanning densitometry (FIG. 5). The protein bands that had been identified in the Western blot as either A or B NP protein were found to comprise approximately 10% to 20% of the total protein in the lysate.

The results of a time-course study done by infecting cells in stationary culture at a multiplicity of infection of 5 pfu/cell and calculating the amount of NP contained in total cell lysates by Western blot indicated that the level of expression for the B NP was greater than that of the A NP. In this experiment, peak production of both NPs occurred 4 to 5 days postinoculation and reached a maximum of 200 to 300 ug NP/$10^8$ cells for the BNP and 50-100 ug NP/$10^8$ cells for the ANP.

The level of expression of the type A NP was lower than that of the type B NP, even though both genes were inserted into the transfer vector in similar orientations. The influenza-specific sequences immediately upstream from the NP initiation codons are different in type A and B viruses and could have different effects on expression levels. Optimum levels of expression have been obtained when the intervening sequences were removed and the initiation codon of the expressed antigen was placed as close as possible to the deleted polyhedrin protein initiation codon on the transfer vector (Matsuura et al., 1987, *Journal of General Virology* 68, 1233-1250).

Antigenic reactivity of baculovirus-expressed NP antigens.

Postinfection mouse serum was prepared by infecting groups of six A/J mice intranasally with $10^5$ $TCID_{50}$ of either influenza B/England/222/82 or A/Ann Arbor/6/60. Serum samples were obtained from each group at 14 days postinfection and pooled.

Adult human serum samples used in this study were from the same set as was used in a previous study with bacterially expressed influenza A NP (Harmon, et al., 1989, *Journal of Medical Virology* 27, 25-30). These serum samples had been obtained during the acute and convalescent stages of illness of patients from whom influenza A or B viruses were isolated. All of these serum pairs used had rises in antibody titer to either influenza A or B detected by hemagglutination inhibition and CF (see Table 1 below, adults 1-13). Serum pairs from infant children which had natural influenza infections as documented by virus isolation (see Table 1 below, children 1 and 2) and from infant children receiving monovalent influenza A vaccine (see Table 1 below, children 3 and 4) were also used. Paired serum samples from adults and infant children with rises in antibody titer to other respiratory viruses (see Table 1 below, adults 14 and 15, children 5 and 6) as well as normal human infant serum (see Table 1 below, children 7 and 8) and normal chimpanzee serum were used as negative controls.

TABLE 1

Comparison of the reactivity of human serum samples with baculovirus-expressed influenza NP antigens with standard diagnostic tests

| | | EIA titre when tested with | | | | Complement fixation fitre | |
|---|---|---|---|---|---|---|---|
| | | Baculovirus-expressed | | | Bacterially expressed | Influenza A | Influenza B |
| Serum | | A NP | B NP | Control | A NP* | virus | virus |
| Rises to influenza A virus | | | | | | | |
| Adult 1 | S1 | 800 | 3200 | 100 | 2560 | <16 | |
| | S2 | 3200 | 3200 | 100 | 10240 | 32 | |
| Adult 2 | S1 | 400 | 3200 | 100 | 640 | <8 | |
| | S2 | 1600 | 1600 | 100 | 2560 | 16 | |
| Adult 3 | S1 | 400 | 200 | 100 | 2560 | 16 | |
| | S2 | 1600 | 600 | 100 | 10240 | 64 | |
| Adult 4 | S1 | 1600 | 800 | 100 | 10240 | 8 | 8 |
| | S2 | 6400 | 1600 | 100 | 40960 | 32 | 8 |
| Adult 5 | S1 | 1600 | 1600 | 100 | 10240 | 8 | 8 |
| | S2 | 6400 | 1600 | 100 | 40960 | 32 | <32 |
| Adult 6 | S1 | 1600 | 1600 | 100 | 10240 | <16 | <8 |
| | S2 | 6400 | 3200 | 100 | 40960 | 32 | <16 |
| Adult 7 | S1 | 1600 | 400 | 100 | 10240 | 8 | <8 |
| | S2 | 6400 | 400 | 100 | 40960 | 32 | <8 |
| Child 1 | S1 | 200 | <100 | <100 | | | |
| | S2 | 1600 | <100 | <100 | | | |
| Child 2 | S1 | <100 | <100 | <100 | | | |
| | S2 | 800 | <100 | <100 | | | |
| Child 3+ | S1 | 200 | <100 | <100 | | | |
| | S2 | 3200 | <100 | <100 | | | |
| Child 4+ | S1 | <100 | <100 | <100 | | | |
| | S2 | 400 | <100 | <100 | | | |
| Rises to influenza B virus | | | | | | | |
| Adult 8 | S1 | 1600 | 200 | 100 | 2560 | <8 | <8 |
| | S2 | 1600 | 25600 | 100 | 2560 | <8 | 128 |
| Adult 9 | S1 | 800 | 400 | 200 | 2560 | <8 | <8 |
| | S2 | 800 | 6400 | 100 | 2560 | <32 | 64 |
| Adult 10 | S1 | 400 | 800 | 100 | 640 | <8 | <8 |
| | S2 | 800 | 6400 | 100 | 640 | <16 | 16 |
| Adult 12 | S1 | 1600 | 400 | 100 | 2560 | 8 | <8 |
| | S2 | 1600 | 25600 | 100 | 2560 | 8 | 512 |
| Adult 13 | S1 | 1600 | 100 | 100 | 2560 | <16 | <16 |
| | S2 | 1600 | 6400 | 100 | 2560 | <16 | 32 |
| Rises to other respiratory viruses | | | | | | | |
| Adult 14 | S1 | 800 | 100 | 100 | | | |
| | S2 | 800 | 200 | 100 | | | |
| Adult 15 | S1 | 800 | 100 | 200 | | | |
| | S2 | 800 | 100 | 200 | | | |
| Child 5 | S1 | <100 | 100 | 100 | | | |
| | S2 | <100 | 100 | 100 | | | |
| Child 6 | S1 | <100 | <100 | <100 | | | |
| | S2 | <100 | <100 | <100 | | | |

TABLE 1-continued

Comparison of the reactivity of human serum samples with baculovirus-expressed influenza NP antigens with standard diagnostic tests

| | EIA titre when tested with | | | | Complement fixation fitre | |
|---|---|---|---|---|---|---|
| | Baculovirus-expressed | | | Bacterially expressed | Influenza A | Influenza B |
| Serum | A NP | B NP | Control | A NP* | virus | virus |
| Normal serum | | | | | | |
| Child 7 | <100 | <100 | <100 | | | |
| Child 8 | <100 | <100 | <100 | | | |
| Chimpanzee | <100 | <100 | <100 | | | |

*Titres from Harmon et al. (1989).
+Monovalent influenza vaccine recipients.

To prepare antigens for EIA assay, Sf9 cells were infected with the recombinant AcNPVs, and the cells were harvested when the cytopathic effect was advanced (usually 4-5 days). The cells were pelleted, washed with Hink's medium, and resuspended in PBS with 1M NaCl. The cells were disrupted by freeze-thawing followed by Dounce homogenization and centrifuged for 1 hour at 10,000×g to pellet cellular debris. Electrophoretic analysis of pellet and supernatant fractions revealed that most of the NP antigen was present in the supernatant.

Lysates of cells infected with a recombinant baculovirus expressing the Lassa fever virus glycoprotein gene (gift of David Auperin and Kimberly Hummel, Centers for Disease Control, Atlanta, Ga.) were prepared as described above and used as negative control antigens.

For EIA, the supernatants were diluted in PBS containing 1% fetal bovine serum and coated onto 96-well polystyrene plates for 24 hours at room temperature. The optimal concentration of the lysates used for coating the plates was a 1:1000 dilution of the BNP lysate and a 1:500 dilution of the ANP lysate containing respectively 3 and 6 µg of protein/ml (approximately 30 ng NP/well) and was determined in assays using the NP-specific monoclonal antibodies to detect bound NP. Wash buffer was PBS plus 0.5% Tween 20. After washing, the plates were preincubated for 1 hour with PBS, 0.5% Tween, plus 1% fetal bovine serum. Dilutions of the serum specimens were then added and allowed to incubate for 2 hours at room temperature. The plates were washed three times, and bound antibody was detected by using Staphylococcal protein A conjugated to horseradish peroxidase with o-phenylene-diamine and hydrogen peroxide as substrate. Titers were expressed as the reciprocal of the highest serum dilution giving a reading of greater than 0.100 in the EIA. Titers listed in Table 1 are the average of duplicate tests on each samples.

Figure 6A:
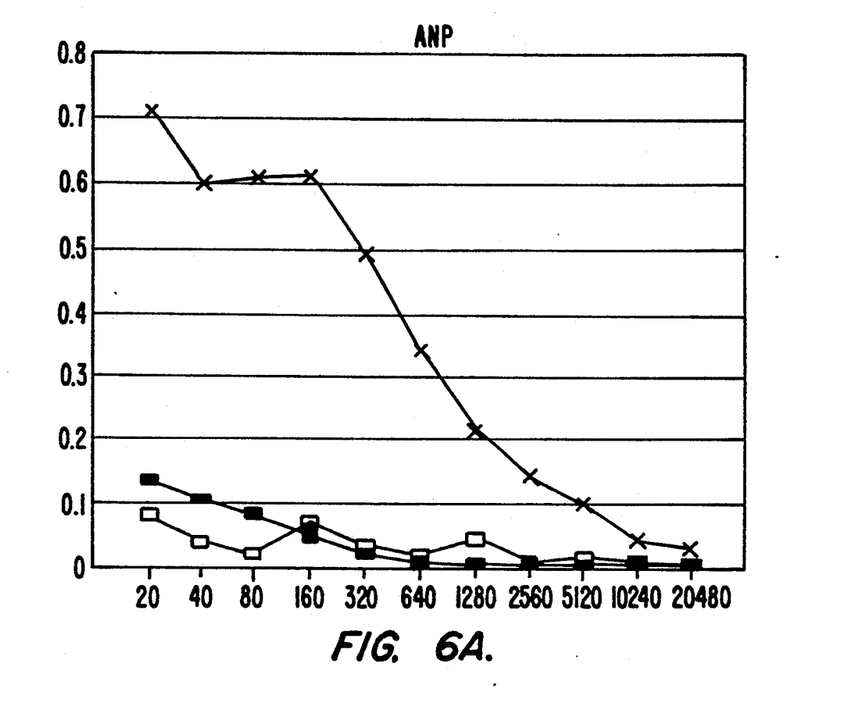
FIG. 6 demonstrates the reactivity of postinfection mouse serum with baculovirus-expressed influenza A or B NP antigens by enzyme immunoassay (EIA). The horizontal axis is serum dilution and the vertical axis is O.D. units after EIA. Open squares represent normal mouse serum, filled squares represent serum from mice infected with type B influenza, and crosses represent serum from mice infected with type A influenza.
Figure 6B:
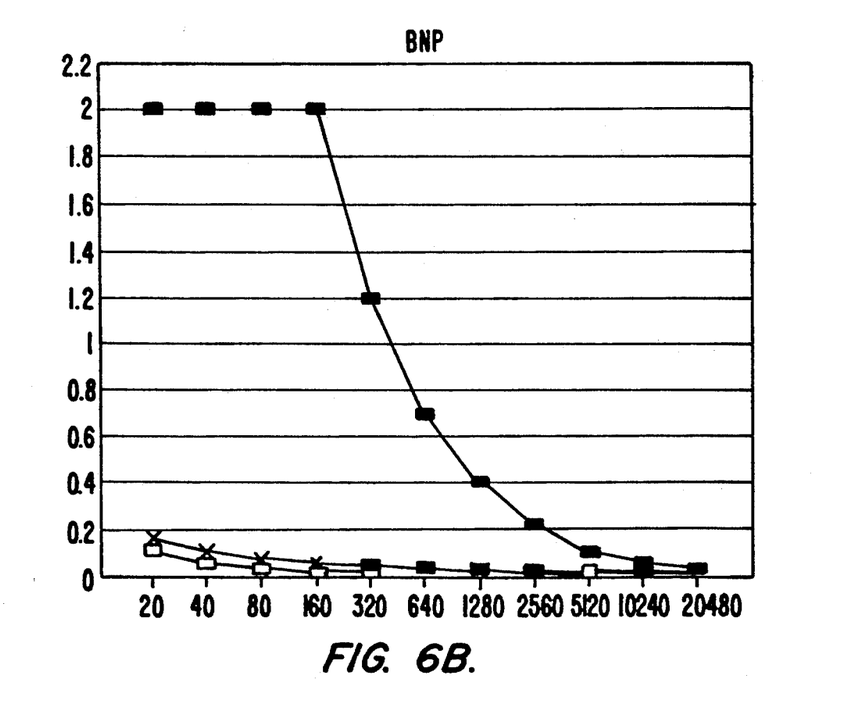

FIG. 6 shows the reactivity of the antigens with serum samples from mice infected with either type A or B influenza. Normal mouse serum showed little background reactivity with either of the test antigens. Serum samples obtained from mice 14 days after infection with influenza virus reacted strongly with the NP antigen of the same virus type used for the infection but not with the NP antigen preparation from the heterologous influenza type. These results indicated that the NP antigens were antigenically reactive when coated onto the EIA plates and that the remainder of the proteins present in the lysate were causing little background reactivity.

The EIA was then tested with a series of acute- (S1) and convalescent-phase (S2) adult human serum pairs that had demonstrated four-fold rises in titer against either influenza A or B as determined by both CF and by hemagglutination inhibition. Table 1 shows that the EIA using the baculovirus-expressed antigens detected serum antibody rises specific for either type A or B influenza.

Figure 7A:
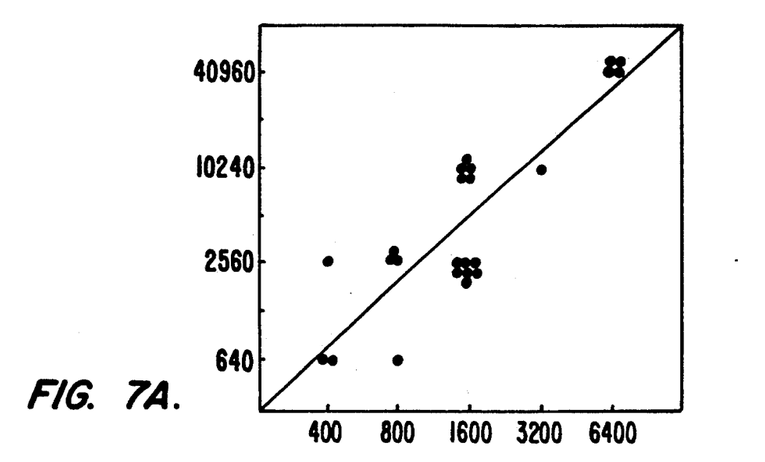
FIG. 7 shows comparison titers obtained in EIA assays using baculovirus-expressed NPs compared to titers obtained using bacterially-expressed ANP or CF. Panel A shows comparison of EIA titers using bacterial (y axis) or baculovirus-expressed (x axis) ANP for 24 serum samples (Table 1, adults 1-7, and 8-13). Panels B and C show comparison of EIA titers (x axis) using baculovirus-expressed ANP (panel B, 24 points, Table 1: adults 1-7, and 8-13) or BNP (panel C, 18 points, Table 1: adults 4-7, and 8-13) NP antigens with titers obtained in CF assays (y axis). Coefficient of correction(r)=0.88(A), 0.58(B), 0.83(C). Level of significance was 0.01 for all panels.
Figure 7B:
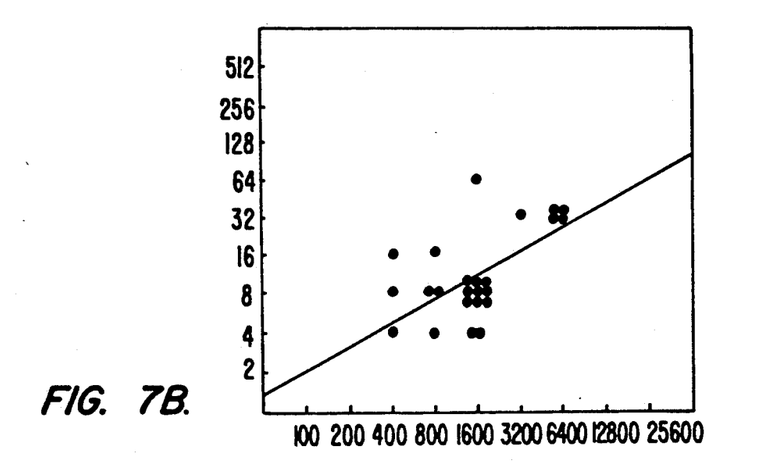
Figure 7C:
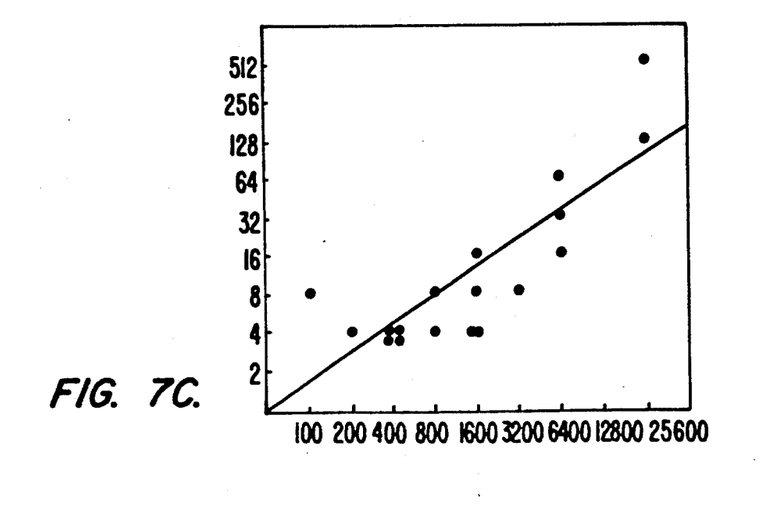
Figure 8A:
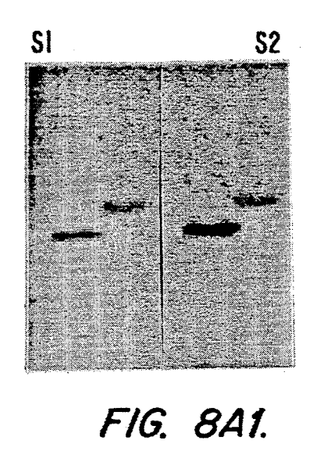
FIG. 8 shows Western blot reactivity of human serum with baculovirus-expressed influenza NP antigens. Lysates of Sf9 cells infected with AcANP (left lanes) or AcBNP (right lanes) were subjected to electrophoresis and transferred to nitrocellulose and hybridized to pairs of acute-phase (S1) and convalescent-phase (S2) human serum specimens that had increased antibody reactivity specifically to either influenza A (A1:Table 1, adult 1, A2: Table 1, adult 5) or influenza B (B:Table 1, adult 8) or to respiratory syncytial-virus (C:Table 1, adult 14).
Figure 8A:
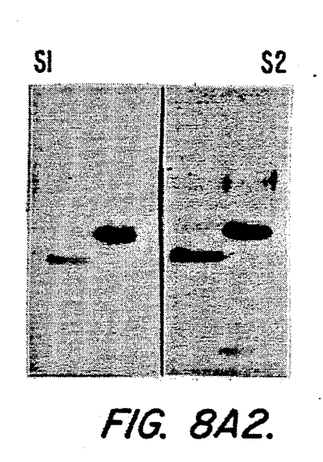
Figure 8B:
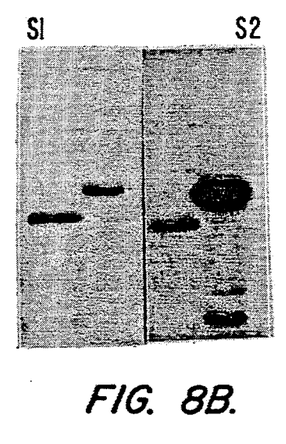
Figure 8C:
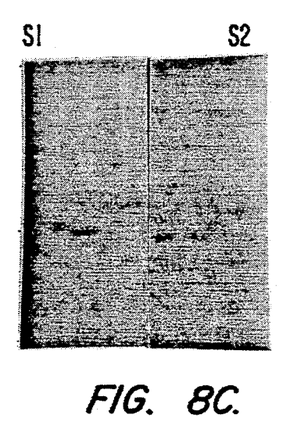

The titers obtained using the baculovirus-expressed ANP antigen showed excellent correlation with titers obtained in assays using highly purified bacterially-expressed ANP (FIG. 7A). The titers obtained using the baculovirus-expressed A and B NP antigens showed a strong positive correlation with titers obtained using the traditional CF assay (FIG. 7B). All of the adult serum pairs that had a four-fold rise in antibody titer against influenza A as detected by CF (Table 1, Adults 1-7) also had a four fold rise in titer when tested with the baculovirus-expressed ANP by EIA.

The EIA using the baculovirus-expressed BNP was slightly more sensitive than CF and for three of the five serum pairs tested detected greater fold rise in antibody titer than did the CF assay (Table 1, Adults 8-13). Also, it appeared that the EIA using the baculovirus-expressed antigens was more sensitive than the CF assay for detecting low levels of antibody in acute serum samples. Of the baculovirus-expressed antigens, the B NP was generally more reactive and gave higher titers than the A NP, even though equivalent amounts of the two antigens were seeded onto the EIA plates.

Many of the acute serum samples from adults reacted both with A and B NP antigens as would be expected for human serum. Control serum pairs from adults that had antibody rises to other respiratory viruses (respiratory syncytial virus and parainfluenza) also showed some reactivity with the influenza A NP antigen. However, eight acute phase or normal serum samples from infant children and one sample from a chimpanzee gave no background reactivity with the baculovirus antigen preparations (Table 1, children 1-8). In addition, EIA plates prepared using lysates of Sf9 cells infected with a polyhedrin-minus recombinant AcNPV showed little background reactivity with any of the human serum samples (Table 1). A polyhedrin-minus baculovirus recombinant was used for the control in these experiments rather than wild-type AcNPV because other investigators have shown that human serum binds non-specifically to the very abundant AcNPV polyhedrin protein. Therefore, the reactivity of the human acute serum samples from adults was most likely due to pre-existing antibody to influenza NP antigens from prior exposure to or vaccination with influenza rather than by non-specific reactivity of the human serum to baculovirus or Sf9 cell antigens.

To further investigate the reactivity of human serum with the baculovirus-expressed influenza NP antigens, lysates of Sf9 cells infected with the recombinant baculoviruses were subjected to SDS-polyacrylamide gel electrophoresis, blotted onto nitrocellulose, and hybridized to several of the human acute- and convalescent-phase (S1 and S2) serum pairs (at 1:200 dilutions) from Table 1.

The Western blot in FIG. 8 confirmed that all the acute serum samples from adults contained antibodies that reacted with NP antigens. In serum pairs that had a previously determined rise in antibody titer to influenza type A, the amount of antibody to the A NP in the convalescent-phase (S2) serum increased visibly relative to the acute-phase serum (S1); the amount of antibody that recognized the B NP remained constant for both serum samples. The reverse was true for the serum pair in which there was a rise in antibody titer to influenza B. The control samples also had detectable levels of NP antibody, but no increase in anti-NP activity was apparent between the acute- and the convalescent-phase serum samples.

Figure 9A:
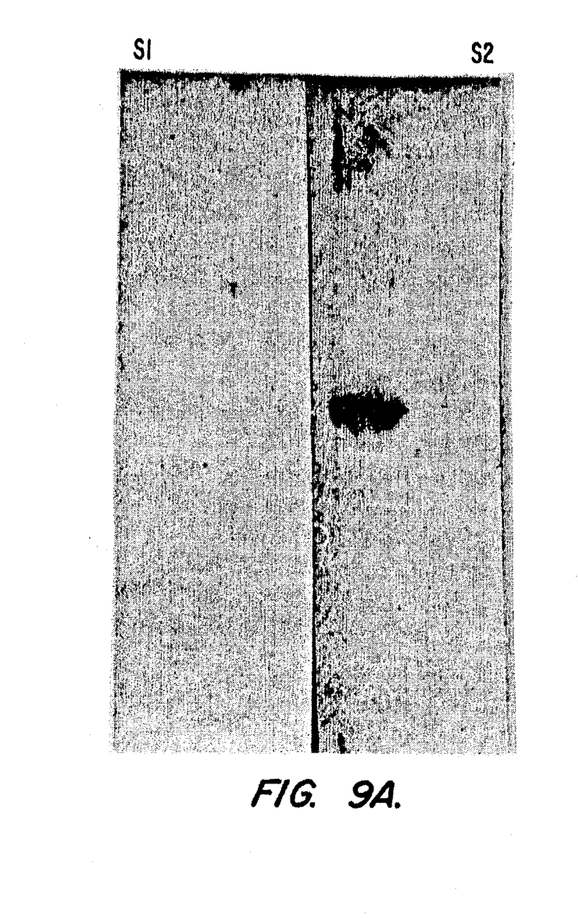
FIG. 9 shows Western blot reactivity of serum from infant children with baculovirus-expressed influenza A and B NP antigens. Acute and convalescent serum pairs (S1 and S2) were from an individual receiving monovalent influenza type A vaccine (A:Table 1, child 3), having a natural influenza type A infection (B:Table 1, child 1) or from a child infected with parainfluenza virus (C:Table 1, child 5). Lysate containing baculovirus-expressed ANP was run in right lane, BNP was run in left lane as in FIG. 8.
Figure 9B:
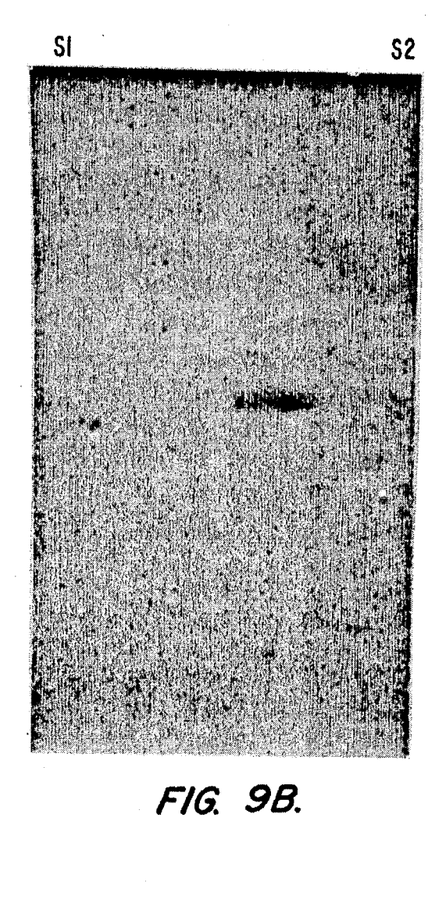
Figure 9C:
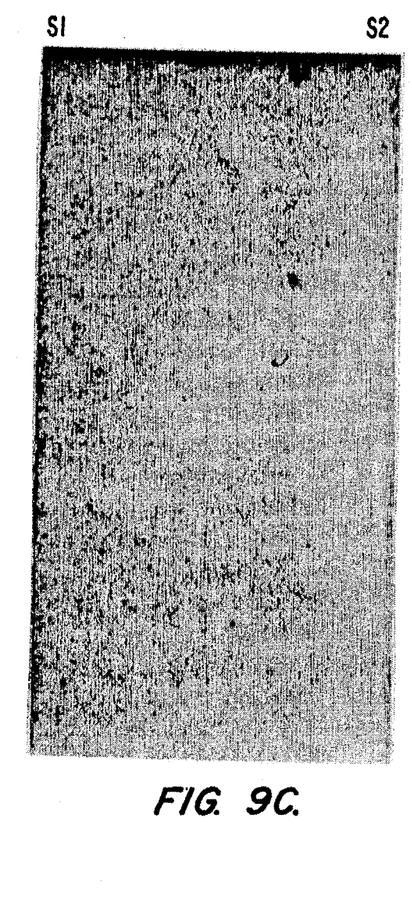

Acute and control serum samples from infant children showed no reactivity with the baculovirus-expressed NP antigens in Western blot assays (FIG. 9). These results confirm that the background from the adult acute serum samples was due to pre-existing antibody and showed that human serum did not react with any of the other proteins contained in these crude baculovirus antigen preparations.

All publication mentioned hereinabove are hereby incorporated by reference.

While the foregoing invention has been described in some detail for purposes of clarity and understanding, it will be appreciated by one skilled in the art from reading of this disclosure that various changes in form and detail can be made without departing from the true scope of the invention.

What is claimed is:

1. A bioassay for the diagnosis of influenza in humans comprising the steps of:
   i) coating a surface with a insect cell lysate comprising the nucleoprotein of influenza A or influenza B;
   ii) contacting said coated surface with a blood sample from a human suspected of having influenza; and,
   iii) detecting the presence or absence of a complex formed between said nucleoprotein and antibodies specific for said nucleoprotein.

2. A bioassay of claim 1 wherein said surface is selected from the group consisting of a polystyrene microtitration plate, a slide and a nylon or nitrocellulose membrane.

3. A bioassay of claim 2 wherein the insect cell is a *Spodoptera frugiperda* cell.

4. A bioassay of claim 2 wherein the insect cell lysate is substantially free of insoluble cellular debris.

5. A bioassay of claim 2 wherein the assay is a Western blot.

6. A bioassay of claim 2 wherein the assay is an immunoblot.

7. A diagnostic kit for detecting influenza in a human blood sample comprising a container containing an insect cell lysate comprising a nucleoprotein of influenza A or B.

8. A diagnostic kit of claim 7 wherein the lysate is substantially free of insoluble cellular debris.

9. A diagnostic kit of claim 7 wherein the cells are *Spodoptera frugiperda* cells.

* * * * *